United States Patent [19]

Gardner

[11] Patent Number: 5,570,426

[45] Date of Patent: Oct. 29, 1996

[54] METHOD AND APPARATUS FOR INTRACRANIAL NOISE SUPPRESSION

[76] Inventor: William A. Gardner, 6950 Yount St., Yountville, Calif. 94599

[21] Appl. No.: 351,004

[22] Filed: Dec. 7, 1994

[51] Int. Cl.⁶ .................... A61F 11/06; H03B 29/00
[52] U.S. Cl. .................... 381/71; 433/27; 381/72
[58] Field of Search .................... 381/71, 94, 72, 381/74, 151; 433/27

[56] References Cited

U.S. PATENT DOCUMENTS

| | | |
|---|---|---|
| 4,153,815 | 5/1979 | Chaplin et al. . |
| 4,403,176 | 9/1983 | Cranston . |
| 5,133,017 | 7/1992 | Cain et al. . |
| 5,140,640 | 8/1992 | Graupe et al. . |
| 5,226,016 | 7/1993 | Christman . |
| 5,278,913 | 1/1994 | Delfosse et al. . |
| 5,295,192 | 3/1994 | Hamada et al. . |
| 5,305,387 | 4/1994 | Sapiejewski . |
| 5,313,945 | 5/1994 | Friedlander . |

*Primary Examiner*—Curtis Kuntz
*Assistant Examiner*—Ping W. Lee
*Attorney, Agent, or Firm*—John P. O'Banion

[57] ABSTRACT

A method and apparatus for active cancellation of vibrational noise produced by a medical instrument in the head of a patient. Vibrations from the instrument, as well as vibrations in the bone structure in the head of the patient, are sensed and processed to generate cancelling noise waves which are then fed into the inner ear through headphones or through vibrators placed on the head of the patient. An equalizer shapes the magnitude and phase spectrum of the vibrational signal picked up from the drill and delivers the equalized signal to the patient. An automatic adaptive controller adjusts the equalizer using control signals consisting of vibrations from the bone structure and the drill.

10 Claims, 6 Drawing Sheets

METHOD AND APPARATUS FOR INTRACRANIAL NOISE SUPPRESSION

BACKGROUND OF THE INVENTION

1. Field of the Invention

This invention pertains generally to noise cancellation methods and devices, and more particularly to a method and apparatus for actively suppressing noise vibrations transmitted from a medical instrument through bone structure and intracranial tissue in the head.

2. Description of the Background Art

In 1844, when Horace Wells introduced anesthesia, including nitrous oxide, and later in 1896 when sulfuric ether was introduced, the discomfort experienced by patients receiving dental health care sharply declined. Today, general anesthesia is considered dentistry's greatest discovery. However, in 1872 when S.S. White Company introduced the first electric drill which was invented by George F. Green, the discomfort caused by drill noise began to increase and continued to do so with further increases in drill speed. The level of discomfort reached a maximum for many patients when the high-speed pneumatic turbine drills were introduced in the 1960's. Today, dentists report that the chief complaint they receive from their patients is—aside from the hypodermic needle—the discomfort from noise caused by either the high-frequency whine of the high-speed (300,000–400,000 maximum RPM) drills or, for some, the chatter and vibration of the so-called low-speed (around 30,000 maximum RPM) drills.

Some reduction of perceived drill noise can be accomplished by muffling the patient's ears, or by using "active headsets" which both muffle the patient's ears and perform noise cancellation of the sound which propagates through the air to the patient's ears. However, even with total suppression of the pressure waves arriving at the ear due to drill noise propagating through the air, dental patients experience only negligible reduction in discomfort because a great deal of the drill noise perceived arrives at the inner ear from propagation paths through the head. That is, the vibration induced in the tooth by the drill enters the bone and propagates along the skull and through the skull interior to the temporal bone and finally to the inner, middle, and outer ears, each of which contributes to the vibrations in the cochlea which are converted to nerve impulses that are sent on to the brain.

Vibrational energy can travel along two different pathways to the cochlea: through the bone, and through the skull interior. Energy transmitted by these pathways is brought together at the temporal bone. From that point, there is a signal line that goes to three separate points of input: (1) the walls of the external auditory canal, (2) the middle ear ossicle, and (3) the cochlear capsule and its contained fluid. In addition, the cochlea has an independent input from the skull interior via what is referred to as the "third window". At each of these points, which represent separate inputs to the outer, middle, and inner ears, respectively, the responses are altered by a number of modifying factors. Specifically, the walls of the external canal radiate sound into its lumen (air), the modifying fact being the external opening, acting as a high-pass filter. The middle ear ossicles respond because of their moment of inertia, this response being modified by the tympanic membrane and the air enclosed in the middle ear, both acting like backsprings. The cochlear capsule undergoes distortional vibrations. The mass of the contained fluid, being unequally distributed, responds in an inertial manner. This cochlear response is modified by the oval and round windows which have not only different compliance values of their own, but face different impedances in the middle ear: the oval window, the ossicular chain; the round window, and the air enclosed in the middle ear.

Finally, along what might be called response line, i.e., the air in the external canal, the tympanic membrane, the ossicular chain, the oval window, and the cochlea, all of these various responses are collected and integrated with one another, according to their phase relationships, and the integrated response finally leads to hair cell stimulation, which creates the nerve impulses that go on to the brain via the auditory nerve.

Some researchers have previously demonstrated that a tone introduced simultaneously into the auditory canal and the skull (using a vibrator pressed against the head), with relative phase and magnitude adjusted properly, would result in no perception of sound in one or the other ear. However, there does not appear to have been any studies of the cancellation of more complex vibrational patterns inside the head. Some researchers have also demonstrated that some degree of reduction in structural vibration can be accomplished through active cancellation techniques. However, no such work on human structures has been found, and prior techniques require access to regions in which zonal nulls are desired.

Therefore, a need exists for a method and apparatus for nulling vibrational noise propagating through the bone structures and intracranial tissue in the head to the inner ear, and more particularly for a method and apparatus which will cancel vibrational noise in the inner ear zones transmitted to a patient from a medical instrument. The present invention satisfies that need, as well as others, and overcomes the deficiencies in prior methods and devices.

SUMMARY OF THE INVENTION

The present invention pertains generally to reducing the discomfort of a patient and the associated exacerbation of perceived pain by suppressing the vibrations propagating through the bone structure and intracranial tissue of the head from a medical instrument using active vibration cancellation and, more particularly, to nulling the vibration waveforms in the inner ear by zonal nulling that results from superposition of electronically processed waveforms with appropriate magnitude and phase relationships. The invention can be used to suppress vibrational noise generated by dental drills, as well as bone cutting tools used in brain and mastoid surgery.

By way of example, and not of limitation, vibrations from the medical instrument, as well as vibrations in the bone structure in the head of the patient, are sensed by accelerometers and processed to generate cancelling noise waves which are then fed into the inner ear through headphones or through vibrators placed on the head of the patient. An equalizer contained in a digital signal processing (DSP) chip shapes the magnitude and phase spectrum of the vibrational signal picked up from the medical instrument and delivers the equalized signal to the patient. An adaptive controller, also contained in the DSP chip, automatically adapts and adjusts the equalizer using control signals consisting of vibrations from the bone structure and the medical instrument.

An object of the invention is to provide for wave superposition inside the subject's head that results in zonal nulls in the two regions containing the left and right inner ears where sound is converted into nerve impulses.

Another object of the invention is to provide for vibration cancellation at the inner ears, which are regions of the body that are inaccessible for the placement of sensors that monitor the degree of suppression.

Another object of the invention is to provide for vibration cancellation using wave-input devices and wave pick-up devices that are comfortable, convenient, and otherwise acceptable by both the dentist or surgeon and the patient.

Another object of the invention is to provide a vibration cancelling method and apparatus that is adaptable to the variety of head characteristics, such as head size and shape and thickness and density of tissue covering bone.

Another object of the invention is to provide for a vibration cancelling method and apparatus that can adapt to the rapidly changing magnitude and phase characteristics of the interface between the medical instrument and the head due to intentional motion of the medical instrument and inadvertent vibration and chatter between the medical instrument and the head.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
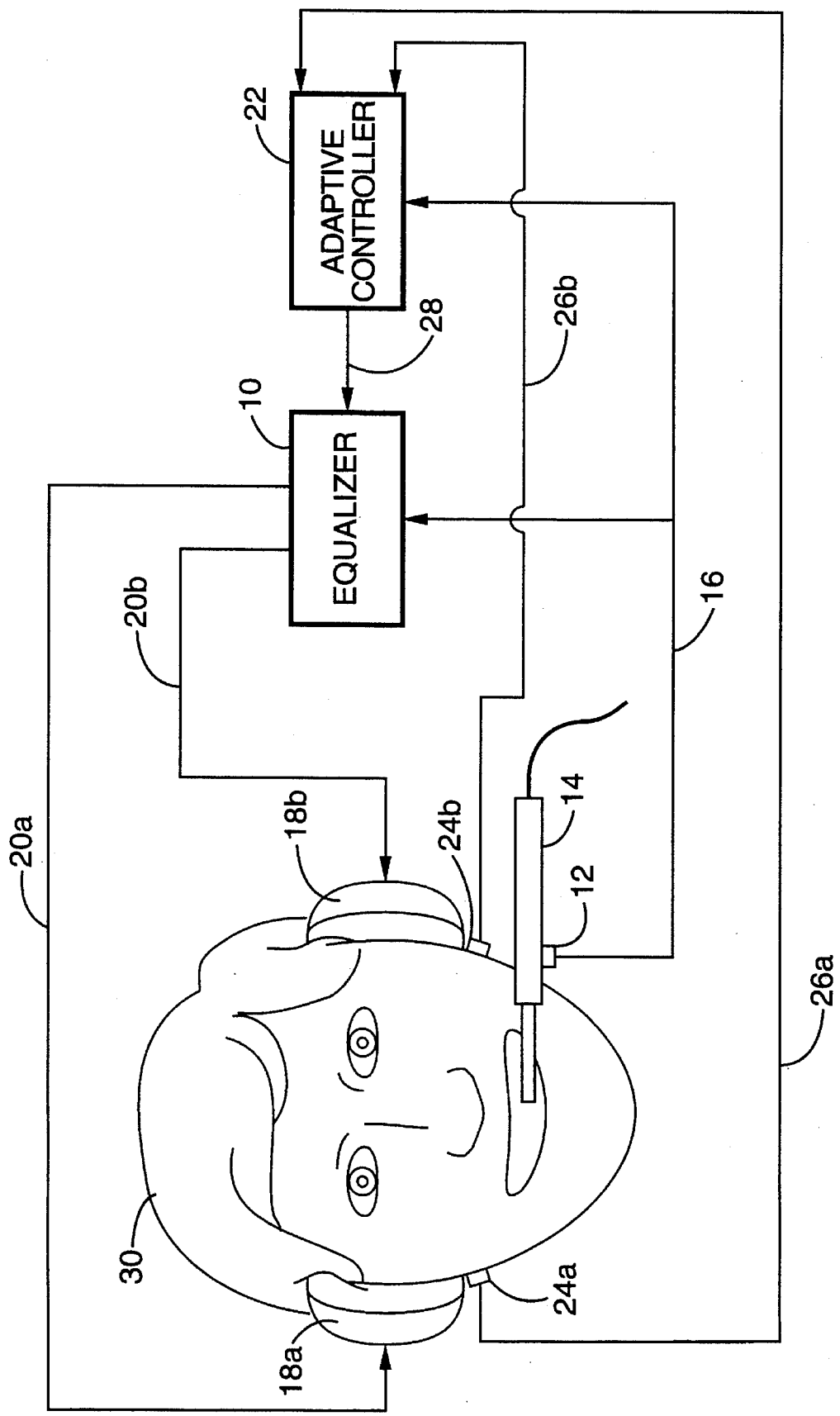
FIG. 1 is a system diagram showing the apparatus of the present invention coupled to a human user and a medical instrument.

Referring more specifically to the drawings, for illustrative purposes the present invention is embodied in the intracranial noise suppression apparatus and method generally shown in FIG. 1 through FIG. 6, as more fully described herein, where like reference numerals denote like parts. It will be appreciated that the apparatus may vary as to configuration and as to details of the parts, and that the method may vary as to the steps and their sequence, without departing from the basic concepts as disclosed herein. It will further be appreciated that, while the drawings depict a dental drill as the source of vibrational noise, the invention can be used with bone cutting tools in connection with brain or mastoid surgery, as well as with other medical instruments which generate intracranial vibrations.

Referring to FIG. 1, the invention includes an equalizer 10 which is electrically connected to a drill vibration pickup 12, such as a conventional accelerometer or the like, which is in turn mechanically coupled to a drill 14. Equalizer 10, the input of which is connected to drill vibration pickup 12 through interconnection 16, shapes the magnitude and phase spectrum of the vibration signal picked up from drill 14 and delivers equalized output signals to a right headphone 18a and a left headphone 18b, to which it is electrically connected through interconnections 20a and 20b, respectively. The invention also includes an adaptive controller 22 which has an input electrically connected to drill vibration pickup 12 through interconnection 16, and inputs electrically connected to right 24a and left 24b mastoid pickups through interconnections 26a and 26b, respectively. Right 24a and left 24b mastoid pickups are conventional accelerometers or the like similar to drill vibration pickup 12. Adaptive controller 22, the output of which is connected to an input of equalizer 10 through interconnection 28, adaptively adjusts equalizer 10 using the vibration signals from drill vibration pickup 12, and right 24a and left 24b mastoid pickups. The adaptively equalized signals emanating from the right 18a and left 18b headphones are acoustically introduced into the patient 30 and cause vibrations in the inner ear.

Figure 2:
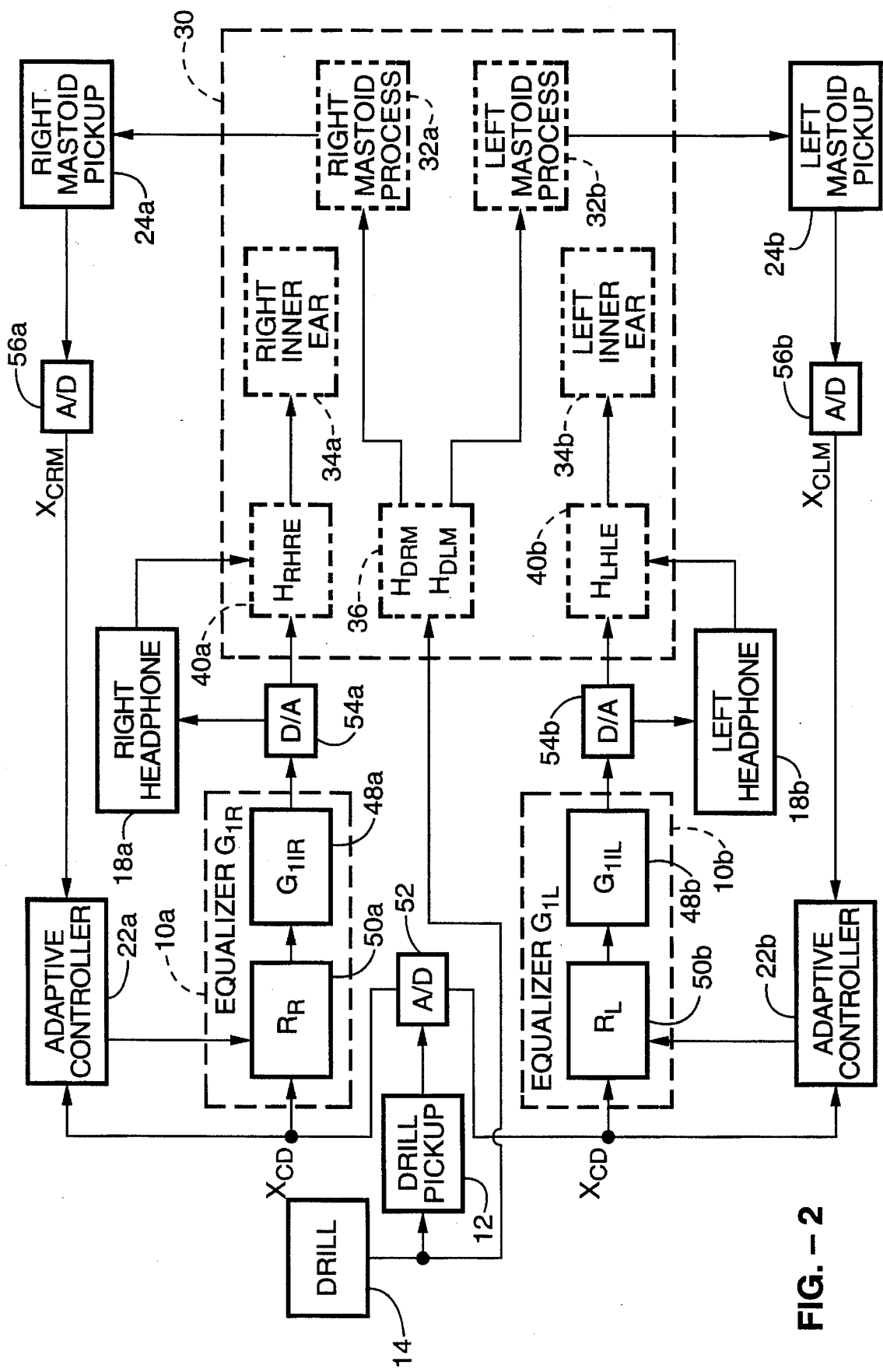
FIG. 2 is a functional block diagram showing the equalizer adaptation process of the apparatus shown in FIG. 1.
Figure 3:
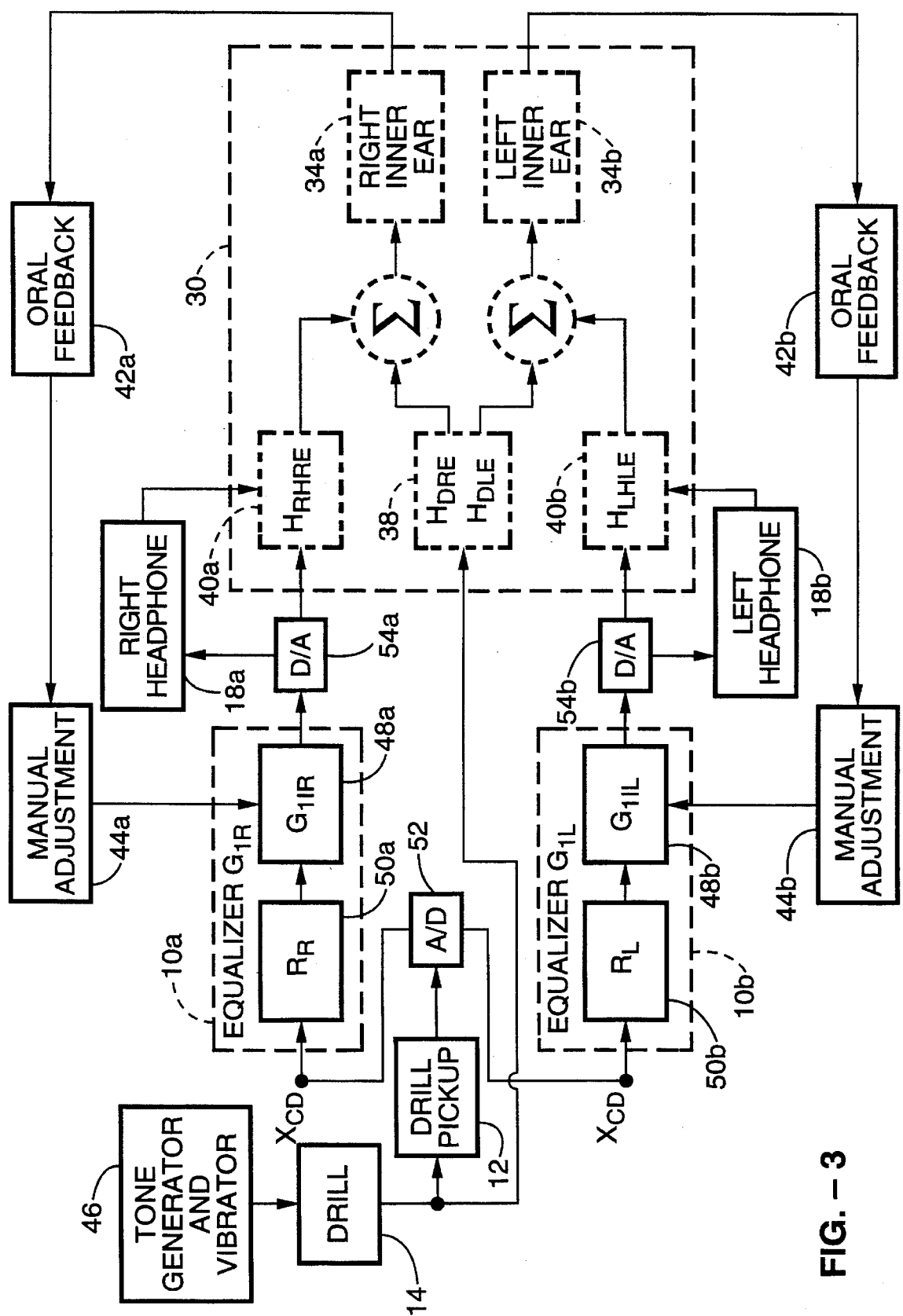
FIG. 3 is a functional block diagram showing the equalizer calibration process of the apparatus shown in FIG. 1.

Referring to FIG. 2 and FIG. 3, the method and apparatus of the invention can be seen in more detail. The relevant model of vibration in the head consists of four parallel channels with transfer functions denoted by H(f), a function of frequency f. These channels are: the channel from drill 14 to the right mastoid process 32a ($H_{DRM}$), the channel from drill 14 to the left mastoid process 32b ($H_{DLM}$), the channel from drill 14 to the right inner ear 34a ($H_{DRE}$), and the channel from drill 14 to the left inner ear 34b ($H_{DLE}$), where $H_{DRM}$ and $H_{DLM}$ are the transfer functions for the physical channels inside the head from the drill to the right 32a and left 32b mastoid processes, respectively, multiplied by the transfer function for the mastoid pickup, and are shown as element 36 in FIG. 2; and where $H_{DRE}$ and $H_{DLE}$ are the transfer functions for the physical channels inside the head from drill 14 to the right 34a and left 34b inner ears, respectively, and are shown as element 38 in FIG. 3. Note that, for simplicity, H(f) has been abbreviated to H. With regard to induced equalized vibrations which enter the ear canals from the headphones, there are two channels of interest: the channel from right headphone 18a to the right inner ear 34a ($H_{RHRE}$), and the channel from left headphone 18b to the left inner ear 34b ($H_{LHLE}$), where $H_{RHRE}$ and $H_{LHLE}$ are the transfer functions from the right and left outer ear to the right and left inner ear times the transfer function for the headphones, respectively, and are shown as elements 40a and 40b, respectively.

Separating the channels in equalizer 10 so as to denote the equalizers for the right 34a and left 34b inner ears as $G_{1R}$ and $G_{1L}$, respectively, which are shown as elements 10a and 10b, the conditions on the equalizers for a null at the right 34a and left 34b inner ears are, respectively, $$G_{1R}H_{RHRE} = -H_{DRE} \tag{1}$$

$$G_{1L}H_{LHLE} = -H_{DLE} \tag{2}$$

The solutions to equations (1) and (2) for equalizers that produce nulls at the two inner ears 34a, 34b are given by $$G_{1R} = -H_{DRE}/H_{RHRE} \tag{3}$$

$$G_{1L} = -H_{DLE}/H_{LHLE} \tag{4}$$

Let Us now consider how the equalizer 10, which can be written as $$G_1 = \begin{bmatrix} G_{1R} \\ G_{1L} \end{bmatrix}, \quad (5)$$

is adaptively adjusted to satisfy the preceding equations by describing in physical terms what the preceding equations state. The vibrations reaching the two inner ears $34a$, $34b$ from the tooth being drilled are cancelled in zones containing the two inner ears by the superposition of the vibrations picked up from the drill casing, and fed through the two individually adapted equalizers $10a$, $10b$ to the headphones $18a$, $18b$. Each equalizer is part of a parallel channel from the drill casing, through the drill vibration pickup, the equalizer, the headphone, and the head or outer and middle ear, to the inner ear.

The adaptation process updates the equalizer $G_1$, relative to an initial setting, by a complex-valued frequency-dependent factor obtained by taking the ratio of the current (locally in time) ratio of the mastoid pickup complex spectrum to drill pickup complex spectrum to the initial ratio of same. Because the left (right) headphone is decoupled from the right (left) ear, the two (left and right) equalizers can be independently adapted. Referring specifically to FIG. 2, let $X_{CD}$, $X_{CRM}$, and $X_{CLM}$ denote complex-valued spectra (functions of frequency f) measured in a current time interval at drill 14 and right $32a$ and left $32b$ mastoid processes, respectively. Separating the channels in adaptive controller 22 into right $22a$ and left $22b$ adaptive controllers, $X_{CD}$ are inputs to right $10a$ and left $10b$ equalizers as well as right $22a$ and left $22b$ adaptive controllers, and $X_{CRM}$ and $X_{CLM}$ are inputs to right $22a$ and left $22b$ adaptive controllers, respectively. $X_{ID}$, $X_{IRM}$, and $X_{ILM}$ denote the same spectra but measured at an initial time interval, during which nulls are obtained by initial manual adjustment of equalizers $G_{IR}$ and $G_{IL}$.

Referring also to FIG. 3, the initial manual adjustment of the equalizers is as follows. The patient 30, or a dental assistant with oral feedback $42a$, $42b$ from the patient 30, manually adjusts a right $44a$ and left $44b$ two-dimensional control to null out a tone heard in the ear and induced simultaneously into the tooth to be drilled via a tone generator/vibrator 46 attached to the drill 14 with the drill casing pressed against the tooth, and through the equalizers $G_{1R}$ and $G_{1L}$ into the two headphones $18a$, $18b$. This is done for each of a set of tones strategically placed throughout the spectral band of the drill noise. This two-dimensional control could be, for example, a lever attached to a ball in a socket (a "joy stick"), or it could be, as other examples, an x-y coordinate control, or a track ball. The two dimensions in which control takes place represent the magnitude and phase of the equalizer at the tone frequency. If a finite impulse response (FIR) structure is used for the equalizer, then this magnitude and phase can be implemented separately, and when the entire set of magnitudes and phases have been determined they can be fit to a transfer function and inverse Fourier transformed to produce the desired FIR impulse response.

If it is still desirable to use masking sound (e.g., music) to maximize the patient's comfort, and if such masking sound is strong enough to be recorded by the mastoid pickup (which is not very likely), then this sound could be time-division multiplexed. That is, this sound could be periodically turned off while adaptation measurements are made. If the off-time is brief enough, the patient will not perceive the periodic absence of the sound. The processed wave that cancels the undesirable vibration in the inner-ear would remain on at all times.

After manual adjustment, the initial equalizer settings $G_{1IR}$ and $G_{1IL}$, shown as elements $48a$ and $48b$, respectively, are updated to current settings as follows:

$$G_{1CR} = G_{1IR} R_R \quad (6)$$

$$G_{1CL} = G_{1IL} R_L \quad (7)$$

where $$R_R = \frac{X_{CRM}/X_{CD}}{X_{IRM}/X_{ID}} \quad (8)$$

and $$R_L = \frac{X_{CLM}/X_{CD}}{X_{ILM}/X_{ID}} \quad (9)$$

$R_R$ and $R_L$ are shown as elements $50a$ and $50b$, respectively. This method takes advantage of the fact that any changes in the drill to inner ear channels should be reflected in the changes in ratios of mastoid and drill spectra. The reason we can use the spectra measured at the mastoid here, rather than the spectra at the inner ear (which are inaccessible), is that these two are related by factors that should exhibit only negligible changes over time.

Thus, the complete process for adaptation of the equalizer is specified by the automatic adaptation of equations (6) through (9), and the manual adjustment procedure by which $G_{1IR}$ and $G_{1IL}$ are initially determined (to produce perceived nulls during the initial time interval). The automatic adaptation is controlled by the right $22a$ and left $22b$ adaptive controllers shown in FIG. 2.

Note also, that the analog output of drill vibration pickup 12 is processed by an analog to digital convertor (A/D) 52 with the digital output thereof being fed into right $10a$ and left $10b$ equalizers and right $22a$ and left $22b$ adaptive controllers, that the digital outputs of right $10a$ and left $10b$ equalizers are processed by right $54a$ and left $54b$ digital to analog convertors (D/A) with the analog outputs thereof being fed to right $18a$ and left $18b$ headphones, respectively, and that the analog outputs of right $24a$ and left $24b$ mastoid pickups are processed by right $56a$ and left $56b$ analog to digital convertors with the digital outputs thereof being fed into right $22a$ and left $22b$ adaptive controllers, respectively. These A/D and D/A convertors are of a conventional type.

Figure 4:
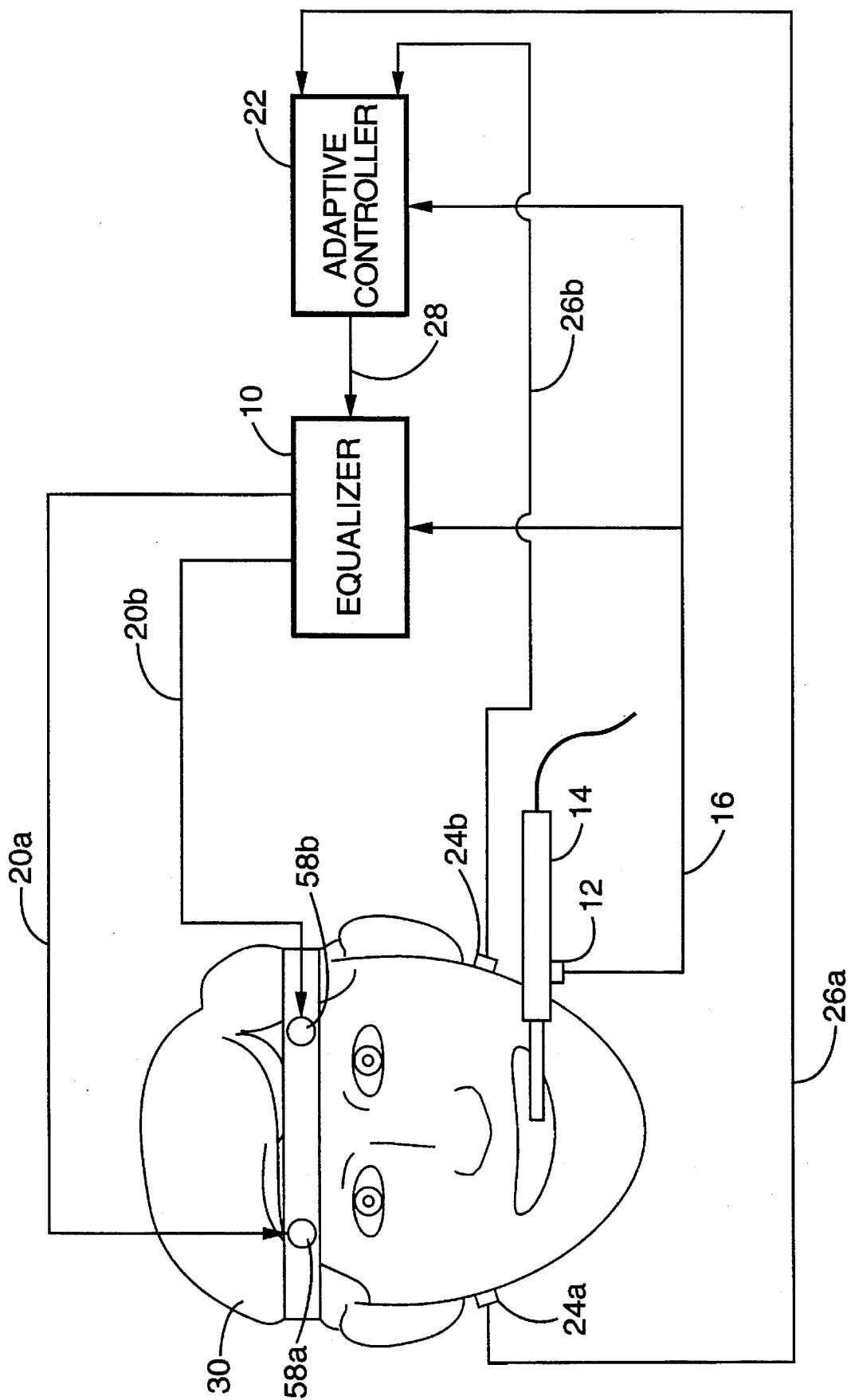
FIG. 4 is system diagram showing an alternative embodiment of the present invention coupled to a human user and a medical instrument.
Figure 5:
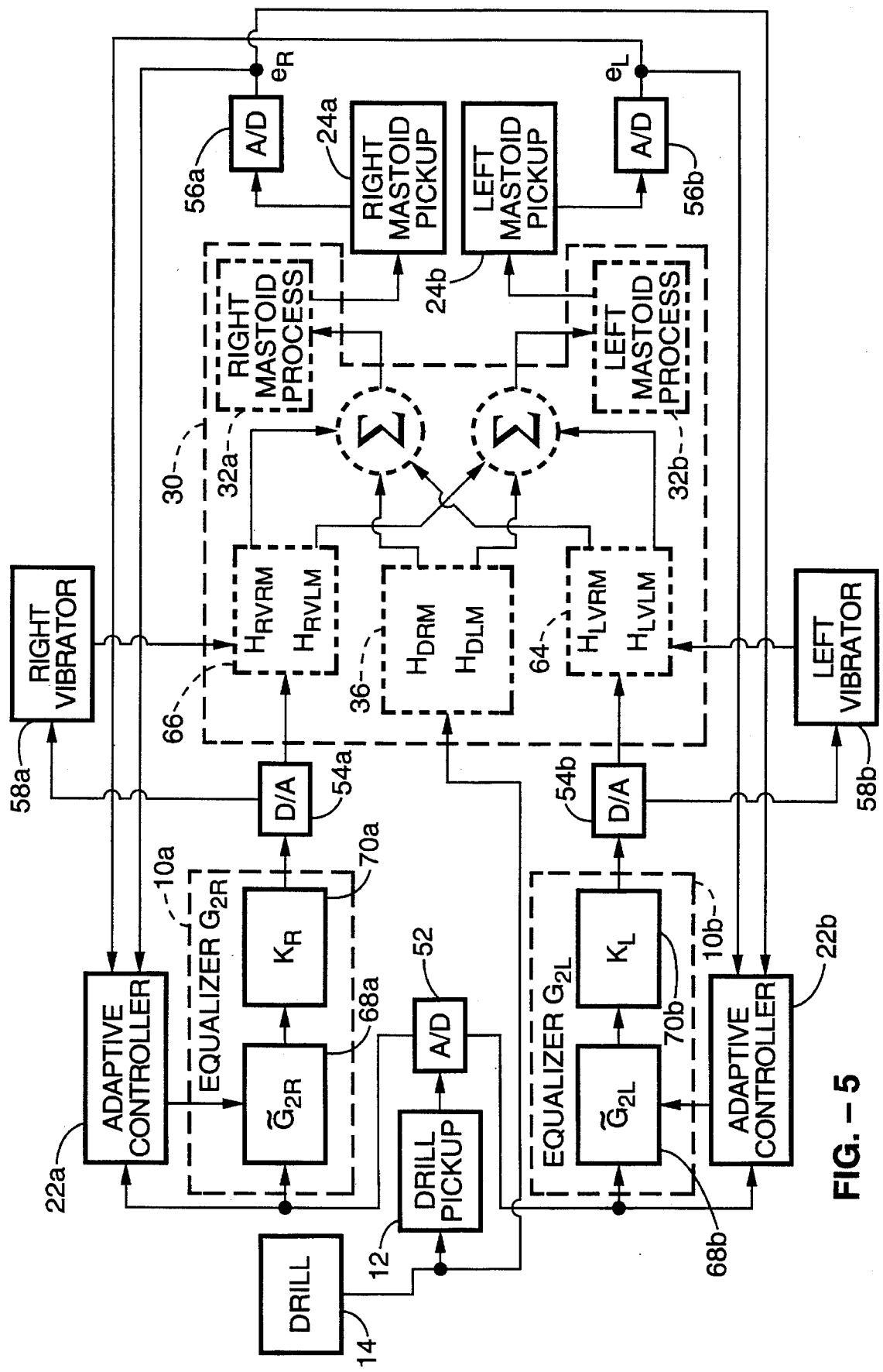
FIG. 5 is a functional block diagram showing the equalizer adaptation process of the apparatus shown in FIG. 4.
Figure 6:
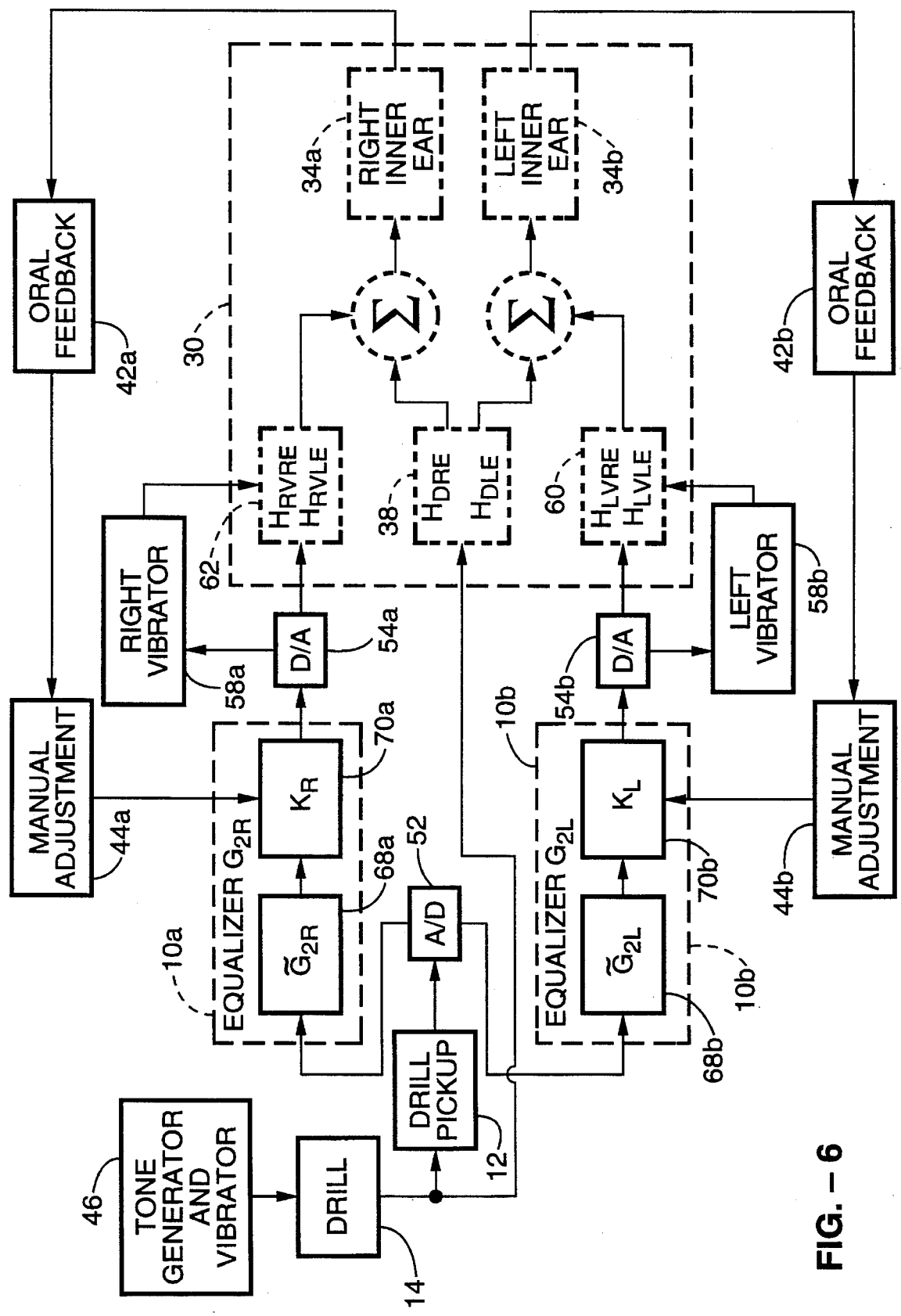
FIG. 6 is a functional block diagram showing the equalizer calibration process of the apparatus shown in FIG. 4.

Referring now to FIG. 4 through FIG. 6, an alternative embodiment is shown in which right $58a$ and left $58b$ head worn vibrators are used for inducing the equalized vibrations through the patient's forehead and into the inner ears instead of using headphones $18a$, $18b$ as previously described. In all other respects, the configuration shown in FIG. 4 is the same as that which is shown in FIG. 1. Here, however, instead of two channels of interest for the induced equalized vibrations, there are eight channels of interest: the channel from the right vibrator $58a$ to the right inner ear $34a$ ($H_{RVRE}$), the channel from the right vibrator $58a$ to the left inner ear $34b$ ($H_{RVLE}$), the channel from the right vibrator $58a$ to the right mastoid process $32a$ ($H_{RVRM}$), the channel from the right vibrator $58a$ to the left mastoid process $32b$ ($H_{RVLM}$), the channel from the left vibrator $58b$ to the right inner ear $34a$ ($H_{LVRE}$), the channel from the left vibrator $58b$ to the left inner ear $34b$ ($H_{LVLE}$), the channel from the left vibrator $58b$ to the right mastoid process $32a$ ($H_{LVRM}$), and the channel from the left vibrator $58b$ to the left mastoid process $32b$ ($H_{LVLM}$), where $H_{LVRE}$, $H_{LVLE}$, $H_{RVLE}$, and $H_{RVRE}$ are the transfer functions from the vibrator location on the skin or tooth through the head to the inner ear times the transfer function for the vibrator, and where $H_{LVRM}$, $H_{LVLM}$, $H_{RVLM}$, and $H_{RVRM}$ are the transfer functions from the vibrator location to the mastoid process times the transfer function for the vibrator times the transfer function for the mastoid pickup. $H_{LVRE}$ and $H_{LVLE}$ are shown as element 60, $H_{RVLE}$ and $H_{RVRE}$ are shown as element 62, $H_{LVRM}$ and $H_{LVLM}$ are shown as element 64, and $H_{RVLM}$ and $H_{RVRM}$ are shown as element 66.

Again, separating the channels in equalizer 10 so as to denote the equalizers for the right 34a and left 34b inner ears as $G_{2R}$ and $G_{2L}$, respectively, which are shown as elements 10a and 10b, the conditions on the equalizers for a null at the right and left inner ears are, respectively, $$G_{2R}H_{RVRE}+G_{2L}H_{LVRE}=-H_{DRE} \tag{10}$$

$$G_{2L}H_{LVLE}+G_{2R}H_{RVLE}=-H_{DLE} \tag{11}$$

On the other hand, if we adapt the equalizers 10a, 10b for nulls at the two mastoid processes 32a, 32b then we satisfy the following conditions:

$$\tilde{G}_{2R}H_{RVRM}+\tilde{G}_{2L}H_{LVRM}=-H_{DRM} \tag{12}$$

$$\tilde{G}_{2L}H_{LVLM}+\tilde{G}_{2R}H_{RVLM}=-H_{DLM} \tag{13}$$

where the notation $\tilde{G}$ indicates that the solution to equations (12) and (13) differs from the solution $G$ to equations (10) and (11). Let us define the following 2×2 matrices and 2×1 vectors:

$$H_{VE}=\begin{bmatrix} H_{RVRE} & H_{LVRE} \\ H_{RVLE} & H_{LVLE} \end{bmatrix} \tag{14}$$

$$H_{VM}=\begin{bmatrix} H_{RVRM} & H_{LVRM} \\ H_{RVLM} & H_{LVLM} \end{bmatrix} \tag{15}$$

$$H_{DE}=\begin{bmatrix} -H_{DRE} \\ -H_{DLE} \end{bmatrix} \tag{16}$$

$$H_{DM}=\begin{bmatrix} -H_{DRM} \\ -H_{DLM} \end{bmatrix} \tag{17}$$

$$G_2=\begin{bmatrix} G_{2R} \\ G_{2L} \end{bmatrix} \tag{18}$$

$$\tilde{G}_2=\begin{bmatrix} \tilde{G}_{2R} \\ \tilde{G}_{2L} \end{bmatrix} \tag{19}$$

Then we can write the solutions to equations (10) through (13) as $$G_2=H_{VE}^{-1}H_{DE} \tag{20}$$

and $$\tilde{G}_2=H_{VM}^{-1}H_{DM}. \tag{21}$$

Let us now define two transfer functions to be the ratios of elements of the vectors in equations (20) and (21):

$$K_R=G_{2R}/\tilde{G}_{2R} \tag{22}$$

$$K_L=G_{2L}/\tilde{G}_{2L} \tag{23}$$

If we adapt the equalizers 10a, 10b to produce nulls at the two mastoid processes 32a, 32b, we get the solution given by equation (21). But, if we put in series with each of these equalizers a corrective equalizer with transfer functions given by (22) and (23), we obtain the composite equalizers $$G_{2R}=\tilde{G}_{2R} K_R \tag{24}$$

$$G_{2L}=\tilde{G}_{2L} K_L \tag{25}$$

which satisfy equation (20) and therefore produce nulls at the two inner ears 34a, 34b.

It should be noted that, neither the mastoid pickup nor any other conceivable and practical pickup can sense directly a null at the inner ear, implying that the right side of equation (20) cannot be measured. This motivates the use of equation (21). Note also that equations (22)–(23) specify conditions for nulls at the inner ears, not an algorithm for finding $K_R$ and $K_L$ (since $G_2$ is not known). $K_R$ and $K_L$ must be determined through manual adjustment.

Let us now consider how the equalizers $\tilde{G}_2$ are adapted using the differential equalizers $$K=\begin{bmatrix} K_R \\ K_L \end{bmatrix} \tag{26}$$

to satisfy the preceding equations. The vibrations reaching the two inner ears from the tooth being drilled are cancelled in zones containing the two inner ears by the superposition of the vibrations picked up from the drill casing, and fed through two jointly adapted equalizers to a pair of vibrators. Each equalizer is part of a parallel channel from the drill casing, through the pickup, the equalizer, the vibrator and the head, to the inner ear. The adaptation minimizes the residual (uncancelled) drill noise appearing nearby the inner ears (at the mastoid processes). If the mismatch between the channels to the inner ears and the parallel channels to the nearby mastoids leaves an unacceptably large residual at the inner ears (when nulls are achieved at the mastoid processes), then manually adjustable equalizers $K_R$ and $K_L$ can be inserted in series with each of the two automatically adaptive equalizers $\tilde{G}_2$. These differential equalizers, collectively referred to as $K$, would compensate for the difference between channels to each inner ear and each mastoid process.

The adaptation method comprises determining $K_R$ and $K_L$ through an initial manual adjustment process, and running an LMS, RLS (recursive least squares), or other type of algorithm to continuously and jointly update the equalizers $\tilde{G}_{2R}$ and $\tilde{G}_{2L}$, which are denoted as elements 68a, 68b in series with $K_R$ and $K_L$, which are denoted as elements 70a, 70b. Although the LMS algorithm can jointly adapt the two (left and right) equalizers, as needed to accommodate cross coupling between left (right) vibrator and right (left) inner ear (and mastoid), this need for joint adjustment complicates the manual adjustment procedure.

To describe the LMS-type of adaptation algorithm, let $x(n)$ denote the digital input to the equalizer 10. The outputs of the automatically adjustable portion of the two equalizers $G_{2R}$ and $G_{2L}$ are $$y_m(n)=\sum_{i=0}^{N-1} w_{mi}(n)x(n-i), \quad m=1,2 \tag{27}$$

where $w_{1i}(n)$ and $w_{2i}(n)$ are the time-dependent (due to adaptation) impulse responses of $\tilde{G}_{2R}$ and $\tilde{G}_{2L}$, respectively. The digitized error signals at the outputs of the right and left mastoid pickups are $e_R(n)=e_1(n)$ and $e_L(n)=e_2(n)$, respectively. The multiple-error filtered-data (MEFD) LMS algorithm (without gradient deflection) can then be expressed as $$w_{mi}(n+1)=w_{mi}(n)-\alpha \sum_{q=1}^{2} e_q(n)r_{qm}(n-i) \tag{28}$$

for m=1, 2 and i=0, 1, 2, . . . , N-1, where $\alpha$ is a step-size parameter, and $r_{qm}(n)$ is the filtered data $$r_{qm}(n)=\sum_{j=0}^{J-1} c_{qmj}x(n-j) \tag{29}$$

where $c_{qmj}$ is the j-th element of the impulse response of the series connection of the drill pickup 12, A/D converter 52, right 70a ($K_R$) or left 70b ($K_L$) manually adjustable differential equalizer, right 54a or left 54b D/A convertor, right 58a or left 58b vibrator, and the internal head channel of patient 30, according to the channel of interest. The corresponding transfer functions are $$C_{11} = K_R V_R H_{RVRM} \quad (30)$$

$$C_{12} = K_R V_R H_{RVLM} \quad (31)$$

$$C_{21} = K_L V_L H_{LVRM} \quad (32)$$

$$C_{22} = K_L V_L H_{LVLM} \quad (33)$$

where $V_R$ and $V_L$ are the transfer functions of the digital to analog convertors. The corresponding four impulse responses for equations (30) through (33) need to be estimated prior to initiation of the MEFD-LMS algorithm. This can be done by using the transfer-function formulas $$C_{11} = E_R/X \quad (34)$$

$$C_{12} = E_L/X \quad (35)$$

with the drill 14 and left vibrator 58b turned off, and x(n) equal to the output from the right vibrator 58a and A/D convertor 52, and $$C_{21} = E_R/X \quad (36)$$

$$C_{22} = E_L/X \quad (37)$$

with the drill 14 and right vibrator 58a turned off, and x(n) equal to the output from the left vibrator 58b and A/D convertor 52. $E_R$, $E_L$, and X are the complex spectra of $e_R(n)$, $e_L(n)$, and x(n).

The step size a should not exceed $$\alpha_{max} = \frac{1}{(<r_{1m}^2> + <r_{2m}^2>)(N+D)} \quad (38)$$

where D is the overall delay from right 54a or left 54b D/A convertor through right 58a or left 58b vibrator to the opposite mastoid pickup.

Since the MEFD-LMS algorithm is well known, a detailed description thereof is not presented herein.

Referring also to FIG. 6, the manual adjustment procedure for $K_R$ and $K_L$ can be exactly the same as previously for $G_{1/R}$ and $G_{1/L}$ described with regard to the apparatus and method of FIG. 1 through FIG. 3, but must be preceded by an initial adaptation of the equalizers $\tilde{G}_{2R}$ and $\tilde{G}_{2L}$ produce nulls at the two mastoid processes. For initial adaptation, $K_R = K_L = 1$, and the transfer functions of equations (30) through (33) must be measured. This can be done by applying a vibrational test signal to the tooth to be drilled via tone generator/vibrator 64 attached to the drill 14 with the drill casing pressed against the tooth, prerecorded drill noise, or another form of test signal that consists of the simultaneous presence of all tones to be nulled during the manual adjustment phase. After the adaptive equalizer $\tilde{G}_2$ has converged (e.g., 1 second after application of the test signal), the patient 30, or a dentist or dental assistant with oral feedback 42a, 42b from the patient 30, can adjust the magnitude and phase of the differential equalizers K (or a model thereof) until the equalized signal passing through the two-preadapted equalizers 68a, 68b, the two vibrators 58a, 58b, and the two differential equalizers 70a, 70b, nulls (at the inner ear) the test signal fed through the tooth to be drilled. In this regard, note that the null is a perceptual null as sensed by the patient in each ear. The manual adjustment phase may take as long as 5 minutes, but can be carried out while waiting for the anesthesia to take effect.

Once differential equalizers 70a, 70b have been adjusted, they need no further adjustment (during drilling) because the differential channel should undergo only negligible change during drilling (provided that the mastoid pickup is physically stationary relative to the inner ear).

After the manual adjustment has been completed, the previously measured transfer functions can be modified as in equations (30)–(33) by multiplication with $K_R$ and $K_L$. Otherwise, they can just be remeasured. Since the accuracy of these measurements is not especially important, the easiest of these two methods to implement should be used. The two transfer functions K determined by the magnitudes and phases learned during manual adjustment can be transformed to two equivalent impulse responses, which can then be implemented as FIR filters. Similarly, the adaptive equalizers $\tilde{G}_2$ can be implemented as FIR filters so that they can be adapted with a least mean square (LMS) type of algorithm, possibly with a convergence-accelerating gradient-deflecting matrix precomputed from typical drill noise or, possibly, adapted during drilling. Note, however, that this gradient deflection might speed up overall convergence but might slow down the suppression of the tonal components of the noise, which might be the most annoying part of the drill noise.

As can be seen, the embodiment of FIG. 1 through FIG. 3 feeds the cancelling noise into the head through headphones 18a, 18b worn by the patient 30 whereas the embodiment of FIG. 4 through FIG. 6 feeds the cancelling noise through vibrators 58a, 58b worn by the patient 30. While the embodiment of FIG. 4 through FIG. 6 uses vibrators placed on the forehead of the patient, other useful input locations for the cancelling noise were found to include teeth other than those being drilled (this is for convenience of the dentist, because the tooth being drilled is also a useful input location for the cancelling vibration), the two mastoid processes, the two temporal bones, the two cheek bones, and the jaw bone, although the jaw bone yielded the weakest sensation at the ear because of the joint between the jaw and the skull. In other words, just about anywhere on the head that bone is close to the skin was found to be a useful location. This is understandable since the dimensions of the head are comparable with the wavelengths in the drill vibration. Nevertheless, the most effective location, in terms of perceived volume of vibration induced on the exterior of the head, was found to be the mastoid processes and the sides of the forehead just in front of the temples. If the mastoid location is used for vibration pick up as in FIG. 3 through FIG. 6, however, this leaves the forehead locations.

The teeth are especially attractive locations for the vibrators, because of their proximity to the source of the drill noise to be suppressed. This results in the largest extent of the zone in which nulling occurs. However, because of the possible bulkiness of sufficiently powerful vibrators, it might be too inconvenient for the dentist and patient to apply these to teeth. If small vibrators with convenient means for attachment to the upper back teeth is deemed possible, this would seem to be the best location from a noise suppression standpoint. Otherwise, the sides of the forehead, just in front of the temple as shown in FIG. 4 seems to be the next best place in terms of providing good coupling to inner ears with minimal delay, minimal cross coupling (left vibrator to right ear), and sufficient distance from error pickups at mastoids.

The most elegant approach, however, was found to be to use headphones 18a, 18b as the transducers to inject the cancelling wave as shown in FIG. 1 through FIG. 3, because this avoids the need for vibrators which may be uncomfortable (due to pressure on the forehead) or which may be inconvenient for the dentist (bulky devices in the mouth). However, this solution does not provide access to any vibration that is proportional in strength to the residual vibration at the inner ear, because the cancelling wave, propagating through the outer and middle ears in this case, does not induce an appreciable vibratory response in the skull, so a mastoid pickup would not sense any effects due to the cancelling noise. Thus, as described above, a different approach to adapting the equalizer is used with the headphone method, as compared with the vibrator method, that does not require measurement of residual vibration. By monitoring the ratio of complex spectra at the drill pickup and the mastoid pickup at each ear, the transfer function of the equalizer for each ear can be updated relative to an initial setting that produced a perceptual null through a manual adjustment procedure.

The embodiment of FIG. 1 through FIG. 3 requires that the mastoid pickups and headphones be kept highly stationary and that the pressure of the mastoid pickup against the skin covering the mastoid be kept very steady. By connecting the pickups rigidly to the headphones, and locating the emitters in the headphones correctly, some compensation for motion might be possible. If, however, due to considerations of patient comfort, necessary body motion renders the requirements for stationary (relative to the inner ear) impractical, the embodiment of FIG. 4 through FIG. 6 described above that uses vibrators placed, for example, on the forehead can be adopted.

With regard to the location of the vibration pick-ups for both embodiments, the best position was found to be that which is closest to the inner ear, with good coupling from the bone surrounding the inner ear; that is, the left and right mastoid processes. Note, however, that with regard to the embodiment of FIG. 4 through FIG. 6, the location for these noise-suppression-error pickups are each about one inch from each of the inner ears, and the wavelengths of vibration in the skull range from a minimum of about two inches at the highest frequencies of interest. Therefore, the correspondence between nulls at the inner ear and the mastoid process might not be precise enough to adequately null out the higher frequencies. This potential problem is circumvented in the embodiment of FIG. 1 through FIG. 3, but it also can potentially be accommodated with the embodiment of FIG. 4 through FIG. 6 as described above. The best impedance matching between skin and pickup can be obtained by using a putty between the pickup and the skin covering the mastoid.

Those skilled in the art will appreciate that the present invention can be implemented using standard analog electronic circuitry or, more economically, standard digital circuitry, including microcomputers. The equalizer 10 and adaptive controller 22 can reside, for example, on a digital signal processor (DSP) chip such as a Texas Instruments TMS320C31 or equivalent. The DSP chip, A/D convertors, D/A converters, and related input/output circuitry are conventional, and can be fabricated on a single DSP board.

Accordingly, it will be seen that this invention provides a method and apparatus for actively cancelling vibrational noise produced by a medical instrument, thereby relieving discomfort and associated exacerbation of perceived pain. Although the description above contains many specificities, these should not be construed as limiting the scope of the invention but as merely providing illustrations of some of the presently preferred embodiments of this invention. Thus the scope of this invention should be determined by the appended claims and their legal equivalents.

I claim:

1. An apparatus for intracranial noise suppression, comprising:

(a) first sensing means for sensing mechanical vibration signals generated by a medical instrument;

(b) second sensing means, configured for attachment to a patient's head, for sensing intracranial vibration signals induced by said medical instrument in the patient;

(c) equalizing means for processing said mechanical and intracranial vibration signals and generating equalizing signals which suppress said intracranial vibration signals;

(d) adaptive controller means for adapting said equalizing means to changes in said mechanical and intracranial vibration signals; and (e) transducing means for transmitting said equalizing signals to said patient.

2. An apparatus as recited in claim 1, further comprising means for calibrating said equalizing means.

3. An apparatus as recited in claim 1, wherein said transducing means comprises headphones coupled to said patient.

4. An apparatus as recited in claim 1, wherein said transducing means comprises vibrators coupled to said patient.

5. An apparatus for suppressing intracranial noise generated by a medical instrument, comprising:

(a) a first accelerometer, said first accelerometer mechanically coupled to a medical instrument;

(b) second and third accelerometers, said second and third accelerometers mechanically coupled to a corresponding one of said patient's left and right mastoid processes;

(c) an adaptively controlled equalizer, said equalizer electrically coupled to said accelerometers, said equalizer including means for generating equalizing signals which suppress intracranial vibration signals generated by said medical instrument;

(d) an adaptive controller, said adaptive controller electrically coupled to said accelerometers and said equalizer, said adaptive controller including means for adapting said equalizing signals to changes in said intracranial vibration signals; and (e) transducing means for transmitting said equalizing signals to said patient.

6. An apparatus as recited in claim 5, further comprising means for calibrating said equalizing means.

7. An apparatus as recited in claim 5, wherein said transducing means comprises headphones coupled to said patient.

8. An apparatus as recited in claim 5, wherein said transducing means comprises vibrators coupled to said patient.

9. A method for suppressing intracranial noise generated by a medical instrument, comprising the steps of:

(a) sensing mechanical vibration signals generated by a medical instrument;

(b) sensing, with a transducer attached to the head of a patient, intracranial vibration signals induced by said medical instrument in the patient;

(c) processing said mechanical and intracranial vibration signals and generating equalizing signals which suppress said intracranial vibration signals;

(d) adapting said equalizing signals to changes in said mechanical and intracranial vibration signals; and (e) transmitting said equalizing signals to said patient.

10. A method as recited in claim 9, further comprising the step of calibrating said equalizing signals.

* * * * *